US011372066B2

(12) United States Patent
Koch et al.

(10) Patent No.: US 11,372,066 B2
(45) Date of Patent: Jun. 28, 2022

(54) MULTI-RESOLUTION QUANTITATIVE SUSCEPTIBILITY MAPPING WITH MAGNETIC RESONANCE IMAGING

(71) Applicant: THE MEDICAL COLLEGE OF WISCONSIN, INC., Milwaukee, WI (US)

(72) Inventors: Kevin M. Koch, Wauwatosa, WI (US); Andrew S. Nencka, Greendale, WI (US); Juan Liu, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 16/968,534

(22) PCT Filed: Feb. 7, 2019

(86) PCT No.: PCT/US2019/017040
§ 371 (c)(1),
(2) Date: Aug. 7, 2020

(87) PCT Pub. No.: WO2019/157174
PCT Pub. Date: Aug. 15, 2019

(65) Prior Publication Data
US 2021/0033688 A1    Feb. 4, 2021

Related U.S. Application Data

(60) Provisional application No. 62/627,335, filed on Feb. 7, 2018.

(51) Int. Cl.
*G01R 33/44* (2006.01)
*G01R 33/56* (2006.01)
(52) U.S. Cl.
CPC ....... *G01R 33/443* (2013.01); *G01R 33/5608* (2013.01)

(58) Field of Classification Search
USPC ........................................................ 324/309
See application file for complete search history.

(56) References Cited

U.S. PATENT DOCUMENTS

2011/0044524 A1* 2/2011 Wang ................. G01R 33/54
382/131
2014/0064590 A1* 3/2014 Imamura ............ G06T 3/40
382/131
(Continued)

FOREIGN PATENT DOCUMENTS

WO    WO-2016209930 A1 * 12/2016    ........... G06T 11/008
WO    WO-2017157872 A1 *  9/2017    ........... G01R 33/443
WO    WO-2017210225 A1 * 12/2017    ........... G01N 24/08

OTHER PUBLICATIONS

Lu, et al., Multiresolution Field Map Estimation Using Golden Section Search for Water-Fat Separation, Magnetic Resonance in Medicine 60: 236-244 (2008). (Year: 2008).*
(Continued)

*Primary Examiner* — Rodneye Fuller
(74) *Attorney, Agent, or Firm* — Quarles & Brady LLP

(57) ABSTRACT

Systems and methods for quantitative susceptibility mapping ("QSM") using magnetic resonance imaging ("MRI") are described. Localized magnetic field information is used when performing the inversion to compute quantitative susceptibility maps. The localized magnetic field information can include multi-resolution subvolumes obtained by segmenting, or dividing, a field shift map. In some instances, a trained machine learning algorithm, such as a trained neural network, can be implemented to convert the localized magnetic field information into quantitative susceptibility data. These local susceptibility maps can be combined to form a composite quantitative susceptibility map of the imaging volume.

20 Claims, 6 Drawing Sheets

(56) References Cited

U.S. PATENT DOCUMENTS

2018/0033144 A1\* 2/2018 Risman .................. G16H 30/20
2018/0180688 A1\* 6/2018 Koch ..................... G01R 33/16

OTHER PUBLICATIONS

K. Jin et al., IEEE Transactions on Image Processing, vol. 26, No. 9, Sep. 2017, 4509-4522.

J. Liu et al., "Quantitative Susceptibility Inversion Through Parcellated Multiresolution Neural Networks and K-Space Substitution", arxiv.org, Cornell University Library, 201 Olin Library Cornell University, Ithaca, NY 14853, Mar. 8, 2019, 1-16.

\* cited by examiner

MULTI-RESOLUTION QUANTITATIVE SUSCEPTIBILITY MAPPING WITH MAGNETIC RESONANCE IMAGING

CROSS-REFERENCE TO RELATED APPLICATIONS

This application is a national stage filing under 35 U.S.C. 371 of International Application No. PCT/US2019/017040, filed Feb. 7, 2019, which claims the benefit of U.S. Provisional Patent Application Ser. No. 62/627,335, filed on Feb. 7, 2018, and entitled "MULTI-RESOLUTION QUANTITATIVE SUSCEPTIBILITY MAPPING WITH MAGNETIC RESONANCE IMAGING," both of which are herein incorporated by reference in their entirety.

BACKGROUND

Quantitative susceptibility mapping ("QSM") is an established, yet growing field of MRI development. QSM is an imaging technique that provides high anatomical contrast and measurements of tissue susceptibility based on biomaterial compositions. As a result, QSM can be advantageously used for monitoring iron overload in diseases such as in Alzheimer's disease; for monitoring demyelinating diseases, such as Parkinson's disease and multiple sclerosis; for monitoring calcifications in the brain and other tissues; and for performing functional MRI. Further applications include monitoring iron overload in the liver and for use in tractography with susceptibility tensor imaging.

QSM, which converts MRI field information into estimates of tissue magnetism, is typically performed using extravagant inversion algorithms. These algorithms seek to invert a known "forward model" dipole convolution that relates the measured axial component of the MRI magnetic field with an isotropic magnetic susceptibility tensor. The inversion is ill-conditioned, and often leads to inaccurate results and spatial "streaking" artifacts. In order to address these issues, iterative QSM algorithms often require substantial computational time to perform the inversion on a case-by-case basis.

In clinically obtained datasets, images are routinely plagued by large heterogeneities and susceptibility variations. In addition, images can suffer from limited scan times and patient motion caused by discomfort. As a result, issues in the tissue masking, phase unwrapping, background field removal, and regularized field inversion algorithms used in susceptibility mapping can be significant, generating regions of large signal fluctuations and poor data consistency. As such, the resulting susceptibility maps are highly subject to streaking artifacts, which severely limits their utility for reliable analysis in the clinic. While modifications and manual processing of these datasets can reduce these issues, ideally an automated, fast, and robust technique would be applied for clinical compatibility.

It would therefore be desirable to provide a method for producing quantitative susceptibility maps that overcomes the drawbacks and limitations of currently existing algorithms. In particular, it would be desirable to provide a method that reduces artifacts in the generated quantitative susceptibility maps, and that is more computationally efficient than currently existing algorithms.

SUMMARY OF THE DISCLOSURE

The present disclosure addresses the aforementioned drawbacks by providing a method for producing a quantitative susceptibility map using magnetic resonance imaging ("MRI"). Magnetic resonance data acquired with an MRI system are provided to a computer system, and a field shift map is generated from the magnetic resonance data using the computer system. The field shift map depicts susceptibility-induced resonance frequency shifts in a volume. The field shift map is processed to generate multiresolution field shift map data containing a plurality of field shift maps each with a different spatial resolution associated with a different resolution layer. For each resolution layer, local field shift map data are generated by dividing the field shift map associated with a given resolution layer into a plurality of local field shift maps. Each local field shift map corresponds to a subvolume of the volume. For each resolution layer, a local susceptibility map is generated for each subvolume by performing a quantitative susceptibility mapping inversion algorithm on each local field shift map associated with a given resolution layer using the computer system. Multi-resolution susceptibility map data are generated by combining the local susceptibility maps for each resolution layer using the computer system. The multiresolution susceptibility map data contain composite susceptibility maps depicting quantitative values of susceptibility in the volume for each resolution layer. A susceptibility map is then generated by combining the plurality of susceptibility maps in the multiresolution susceptibility map data.

It is another aspect of the present disclosure to provide a method for producing a quantitative susceptibility map using MRI and a trained machine learning algorithm. Magnetic resonance data acquired with an MRI system are provided to a computer system, and a field shift map is generated from the magnetic resonance data using the computer system. The field shift map depicts susceptibility-induced resonance frequency shifts in a volume. The field shift map is divided by the computer system into a plurality of local field shift maps, where each local field shift map corresponds to a subvolume of the volume. A trained machine learning algorithm is provided to the computer system where it is implemented with a hardware processor and memory of the computer system. The trained machine learning algorithm is a machine learning algorithm that has been trained on training data including a plurality of subvolume training data sets that are similarly sized as the plurality of local field shift maps. The training data store susceptibility-induced resonance frequency shift values. The local field shift maps are applied to the trained machine learning algorithm in order to generate with the computer system a local susceptibility map for each subvolume. A composite susceptibility map is formed by combining the local susceptibility maps using the computer system. The composite susceptibility map depicts quantitative values of susceptibility in the volume.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
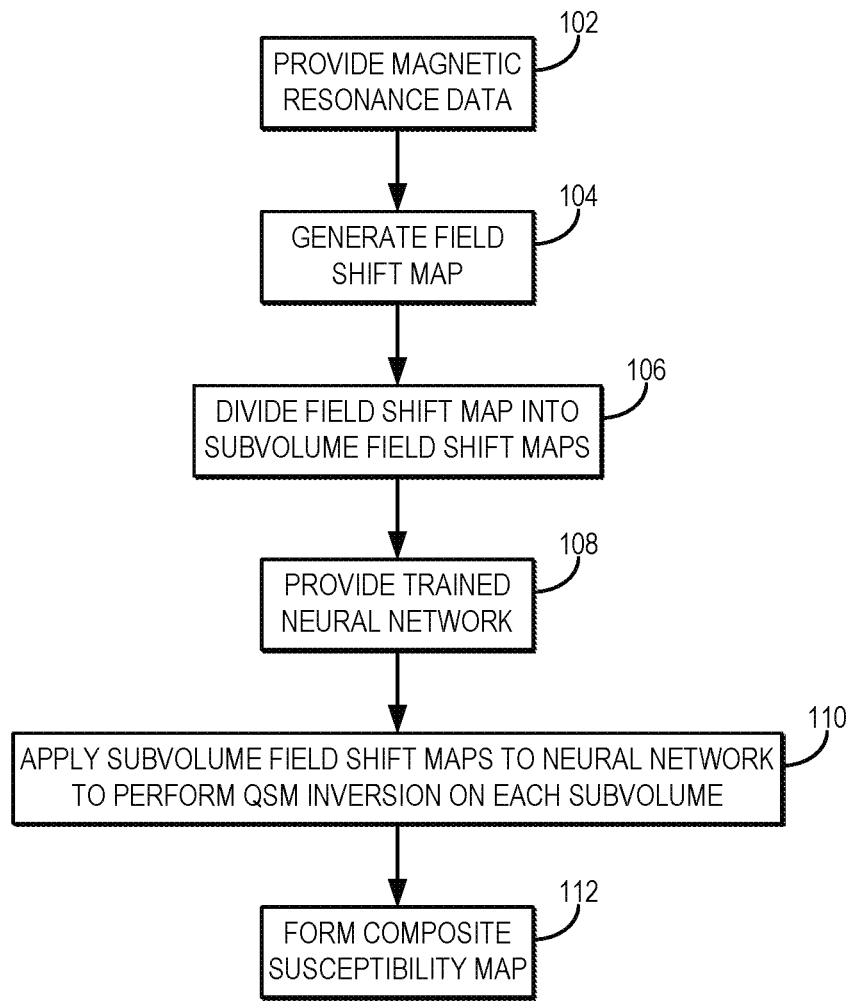
FIG. 1 is a flowchart setting forth the steps of an example method for generating a quantitative susceptibility map using localized processing of a field shift map based on a machine learning algorithm implemented with a hardware processor and memory that takes as input parcellated field shift maps.

Described here are systems and methods for quantitative susceptibility mapping ("QSM") using magnetic resonance imaging ("MRI") and multiresolution, localized magnetic field information for performing the inversion to compute quantitative susceptibility maps. The methods described in the present disclosure can also be applicable to other source inversion problems in medical imaging, such as those encountered in magnetoencephalography ("MEG") and MRI-based impedance mapping.

In some embodiments, the localized magnetic field information can be obtained by segmenting a field shift map into multiple subvolumes, or parcels, of local field perturbations in each of a plurality of different resolution layers. In particular, the field shift map can be processed to generate multiresolution field shift map data containing the field shift map converted to different spatial resolutions associated with the different resolution layers. Each field shift map in each resolution layer can then be segmented into parcels having different resolutions. The multi-resolution, parcellated field shift maps can then be processed using established QSM algorithms. Following their independent processing, the individual parcels are combined to form a composite image, or quantitative susceptibility map, in each resolution layer and the resulting multiresolution susceptibility maps can be combined to form a susceptibility map for the subject. Advantageously, using a multi-resolution approach allows parcels to be scaled between resolutions when estimating susceptibility.

In some other embodiments, a neural network or other machine learning algorithm can be trained using parcels of data that are similar (e.g., similar in size) to the parcellated field shift map, whether multi-resolution parcels are used or parcels with a single common resolution. The training data used to train the neural network or other machine learning algorithm can include magnetic resonance data acquired from the same subject or previously acquired data from another subject. The training data can also be simulated data, such as electromagnetic ("EM") simulation data. In these instances, the training data may also include simulated data based on more than one different forward model. The training data may also include or be based on random or pseudorandom susceptibility volumes.

The training data may be multi-resolution training data, and the neural network or other machine learning algorithm is trained to the different resolutions and parcel sizes. Training of the neural network or other machine learning algorithm may, therefore, include training a different neural network or machine learning algorithm on each of the different resolution sizes, or may include training a single neural network or other machine learning algorithm on more than one of the different resolution sizes.

In still other embodiments, the entire volume can be processed, or a single subvolume can be processed without dividing the field shift map into multiple different subvolumes. In these instances, the output will be a susceptibility map that is displayed to a user or otherwise stored for later use. For these implementations it is preferable to use a graphics processing unit ("GPU") or other processor or computer system with sufficient memory to processes the entire field shift map volume.

Using the techniques described in the present disclosure, residual streaking artifacts in the composite susceptibility map are constrained to the individual volumes from which they originate, thereby eliminating their propagation through the image. By parcellating the field shift map, the computational efficiency of the QSM algorithms can also be improved, such as by distributing the independent QSM inversion for the individual parcels across multiple computer processors or by utilizing computationally efficient neural networks or other machine learning algorithms. Using the multi-resolution techniques described in the present disclosure also allows for scaling of parcels between resolutions when estimating susceptibility, which can further improve computational efficiency without loss of spatial resolution.

Another benefit of the systems and methods for localized QSM described here is their ability to achieve real-time QSM. Because of the efficiencies provided by the localized QSM techniques described here, optimizations can be performed in significantly less time that currently available QSM techniques, which indicates that real-time QSM is viable. Advantageously, the systems and methods for localized QSM described here can be employed with any of the currently available algorithms used for generating quantitative susceptibility maps.

Referring now to FIG. 1, a flowchart is illustrated as setting forth the steps of an example method for producing a quantitative susceptibility map using parcellated volume processing and an appropriately trained neural network or other machine learning algorithm to take advantage of localized field shift information for computing regional susceptibility distributions. The method includes providing magnetic resonance data to be processed, as indicated at step 102. As one example, the magnetic resonance data can be provided by retrieving previously acquired data from data storage. As another example, magnetic resonance data can be acquired with an MRI system and provided to a computer system, such as the MRI system workstation or other suitable computer system, for processing. In either case, the magnetic resonance data are suitable for generating quantitative susceptibility maps. For instance, the magnetic resonance data can include susceptibility-weighted data acquired using a suitable pulse sequence, such as a $T_2^*$-weighted pulse sequence or other pulse sequence capable of producing enhanced image contrast in areas with different susceptibility than surrounding tissue. In some instances, the magnetic resonance data can include images that are reconstructed from k-space data acquired with the MRI system and, thus, providing the magnetic resonance data may in some instances include reconstructing such images from k-space data.

The provided magnetic resonance data are then processed to generate a field shift map, as indicated at step 104. The field shift map, δ, indicates regions where field offsets resulting from significant differences in local magnetic susceptibility are present in the subject that was imaged. The field shift map, δ, is then divided, or parcellated, into a number of field shift subvolumes, $\delta_k$, as indicated at step 106. As an example, the field shift map can be a data structure stored in a computer memory, such as an image matrix. In such instances, the subvolume field shift maps can include data structures stored in a computer memory, such as image matrices corresponding to those pixels or voxels in the field shift map that are associated with the subvolume.

Figure 2:
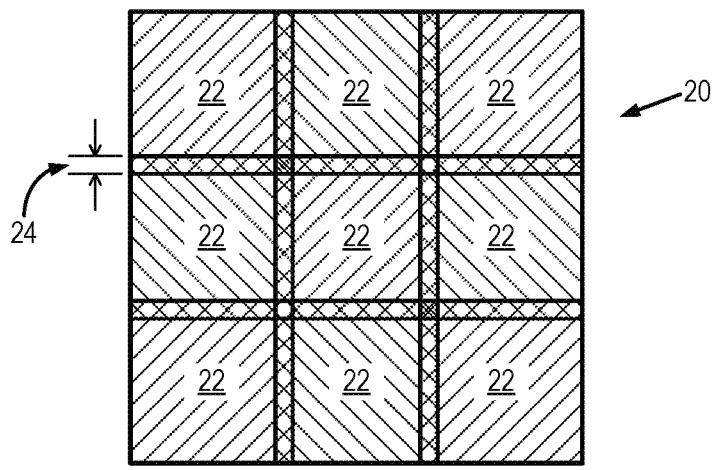
FIG. 2 illustrates an example of subdividing an acquisition or image volume into a plurality of overlapping subvolumes, or parcels.

Referring now to FIG. 2, for the parcellation of the field shift map the image volume 20 associated with the field shift map is divided into a plurality of subvolumes 22 that are each smaller than, and contained within, the original image volume 20. Preferably, these subvolumes 22 are at least partially overlapping, as indicated by overlapping regions 24. By overlapping the subvolumes 22, local field effects can be more reliably accounted for during the inversion process used to generate the quantitative susceptibility maps. As one example, the field shift map is divided into regularly-spaced and overlapping volumetric parcels. The overlap distance can be selected as follows, $$z_t = \left(a^3 \frac{2}{3} \frac{B_0}{B_{min}} \Delta \chi_{max}\right)^{1/3}. \quad (1)$$

which the threshold distance, $z_t$, at which the field perturbation from a susceptibility source provides negligible contribution to the Larmor frequency-offset.

For a target parcel volume-of-interest, additional spatial-frequency information up to the threshold distance, $z_t$, can be padded for each principle direction prior to solving for the local susceptibility. By including this extra spatial frequency-offset information in the QSM optimization, all local susceptibility sources with significant contribution to the frequency information within the parcel volume will be included in the net susceptibility calculation.

Referring again to FIG. 1, the method also includes providing a trained neural network or other machine learning algorithm, as indicated at step 108. The trained neural network or other machine learning algorithm can be implemented on a hardware processor and memory, and is trained on training data that are similar to the subvolume field shift maps produced in step 106. For instance, the training data can include parcels of data having similar size and resolution to those produced in step 106. As mentioned above, the training data can include parcellated field shift maps based on data acquired from the same subject as the magnetic resonance data provided in step 102, parcellated field shift maps obtained from a different subject, an average of parcellated field shift maps obtained from a population of subjects, EM simulation data including parcellated field shift maps simulated using one or more different forward models, or random susceptibility volumes.

As noted, as one example, the machine learning algorithm that is trained can include a neural network. The neural network can be a convolutional neural network or other type of artificial neural network. In either case, the neural network is generally constructed as a model of interconnected neurons that characterize the problem at hand. These neurons are mathematically represented by weight and bias coefficients connected via a set of operations, such as convolutional (e.g., spatial filtering) operations in the case of a convolution neural network. In the methods described in the present disclosure, the neurons connect an input magnetic field distribution with an output magnetic susceptibility distribution. In some instances, the neural network can also be an encoder-decoder neural network. The use of an encoder-decoder network allows for implicit application of the aforementioned multi-resolution decomposition through multiple connected layers of spatial convolution and deconvolution. Machine learning algorithms other than neural networks can also be implemented, such as support vector machines ("SVM") and other algorithms based on supervised learning, unsupervised learning, deep learning, ensemble learning, dimensionality reduction, and so on.

For those instances where a neural network is trained, the training data are used to determine the weights and biases that characterize each layer of the neural network. As mentioned above, the training data may include simulation data generated based on a computational model of known susceptibility distributions and source magnetic fields. By randomly generating susceptibility distributions, magnetic fields can be computed using a Fourier-driven relationship between the two fields.

In the methods described in the present disclosure, training of the neural network, or other machine learning algorithm, takes advantage of dimensionality reduction, in which the neural network or other machine learning algorithm is divided into manageable pieces that can be independently processed. In particular, the neural network or other machine learning algorithm is trained on parcellated subvolumes and the corresponding input to the neural network or other machine learning algorithm includes similarly sized parcellated subvolumes.

The subvolume field shift maps are provided to the trained neural network, or other machine learning algorithm, to perform QSM inversion and produce quantitative susceptibility maps for each of the subvolumes, as indicated at step 110. The parcel maps generated in this process thus represent quantitative susceptibility maps corresponding to regions of local susceptibility, $\chi_k$, associated with the subvolumes, $V_k$.

The quantitative susceptibility maps for the different subvolumes are then combined to form a composite quantitative susceptibility map, as indicated at step 112. This composite quantitative susceptibility map represents a measurement of the magnetic susceptibility in the subject that was imaged, thereby indicating a spatial distribution of magnetic susceptibility in the subject. The composite susceptibility map can be a data structure stored in a memory, such as an image matrix whose pixels or voxels store quantitative magnetic susceptibility values for different spatial locations in an imaging volume. The composite susceptibility map can be stored for later processing and use, and can also be provided to a display for a clinician or other user.

As one example, the individual parcel maps can be stitched together to form the composite map. The stitching procedure may include scaling the parcel maps, adjusting mutual information of the overlapping regions of the parcel maps, and adjusting the dynamic range of the parcel maps.

In one embodiment, the stitching procedure includes discarding the overlapping regions and combining the parcels to produce a composite susceptibility map exhibiting distinct boundaries between adjacent parcels. To remove this effect, a linear gradient is applied along the overlapping sections during the parcel combination process. This approach weights the value of an individual voxel based on its proximity to the target parcel volume. Combining all parcels and their weighted overlapping regions, a smoother and cleaner composite susceptibility map can be produced.

It should be appreciated by those having ordinary skill in the art, however, that any number of suitable techniques for stitching or otherwise combining the individual parcel maps can be implemented.

Figure 3:
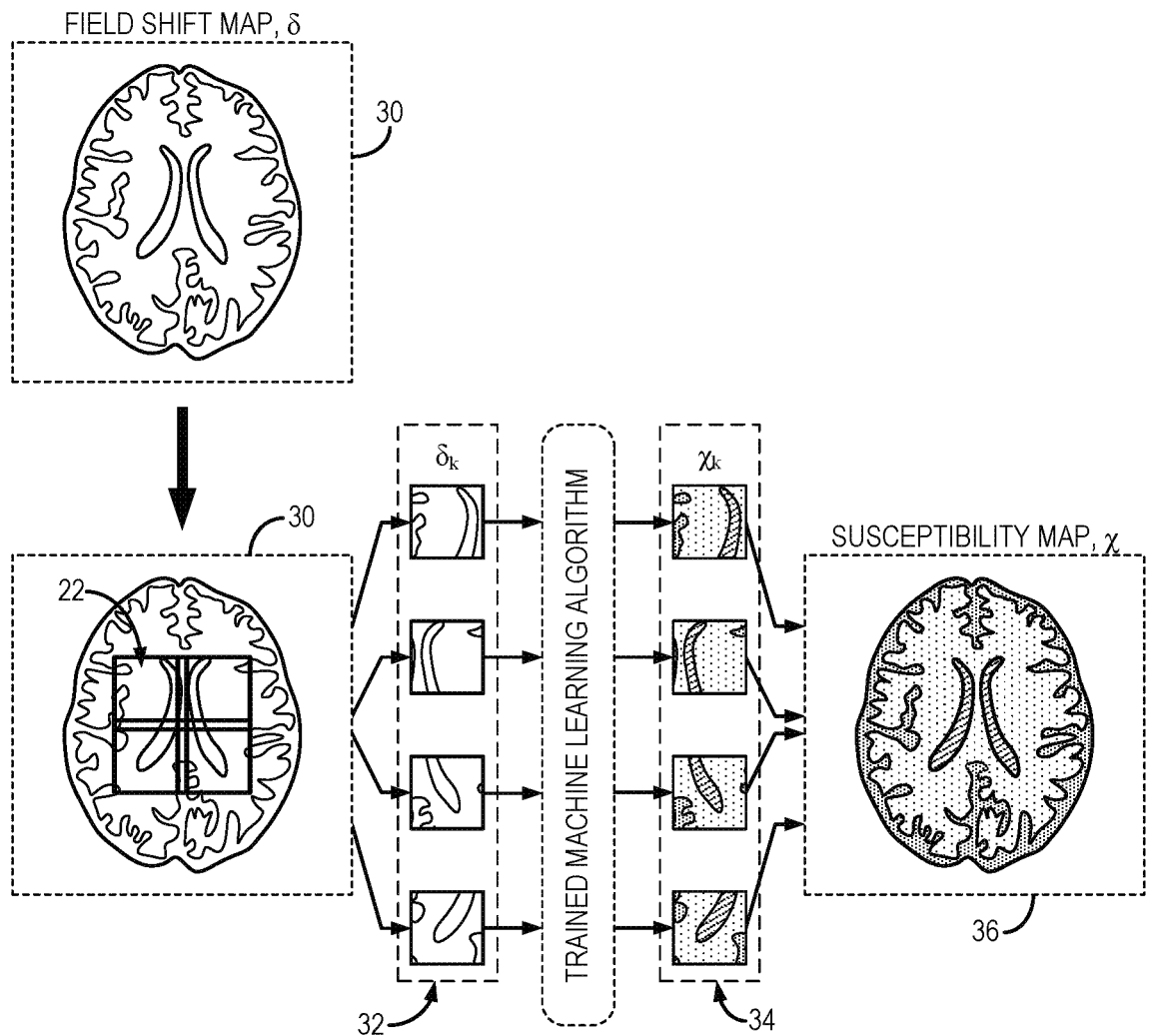
FIG. 3 is a schematic illustration of the method for generating a quantitative susceptibility map shown in FIG. 1.

The foregoing method is schematically illustrated in FIG. 3, where a field shift map 30, $\delta$, is divided into volumetric parcels 22 to create local field shift maps 32, $\delta_k$. For the sake of clarity, only four such volumetric parcels 22 are illustrated in FIG. 3; however, the entire volume is preferably divided into volumetric parcels 22. The local field shift maps 32, $\delta_k$, are then applied to a trained neural network, or other machine learning algorithm, as described above to generate local susceptibility maps 34, $\chi_k$, associated with the volumetric parcels 22. As mentioned above, the neural network or other machine learning algorithm is trained on data including subvolumes of similar size as local field shift maps 32, $\delta_k$. The local susceptibility maps 34, $\chi_k$, are then stitched together, or otherwise combined, to form a susceptibility map 36, $\lambda$, corresponding to the entire volume.

In one non-limiting example, a training set of 5000 8×8×8 voxel parcels was used to train a neural network that included six layers. The layers of the neural network included 128*512, 64*512, 32*512, 16*512, 8*512, and 512 individual neurons, resulting in over 127,000 neurons. This example neural network had regional neural connectivity determined by successive convolutional filters of 2×2×2 kernels.

Training of the neural connections in this non-limiting example was performed using random batches of 64 training sets across 500 epochs. Within each epoch, the neurons were trained through a cost function optimization routine connecting the input and output training sets. As one example, an Adam iterative optimization algorithm, which is a stochastic gradient descent optimization routine, can be used.

Although the training process can take several minutes or hours, the neural network or other machine learning algorithm generally needs to be trained only once. The subsequent use of the trained neural network or other machine learning algorithm requires significantly less time to produce the subvolume susceptibility maps, especially compared to current iterative QSM algorithms. The methods described in the present disclosure have the added benefit that more reliable estimation of susceptibility values can be obtained in datasets with relatively sharp discontinuities between adjacent voxels, especially when compared to QSM algorithms that implement discrete transformations.

The methods described in the present disclosure can also be used as a secondary training and application step to remove DC biases from parcels, which may otherwise be present when using a parcellated volume approach to QSM inversion.

The methods described in the present disclosure can also be applied to preprocessing steps common to QSM, such as field map generation and background removal. In these instances, a single neural network or other machine learning algorithm can be constructed to take a collection of complex MRI images and then produce a susceptibility distribution estimate, rather than take background-removed field shift maps as input data. As an alternative embodiment, a single network can accept raw field maps and simultaneously perform background removal and susceptibility distribution estimation.

Figure 4:
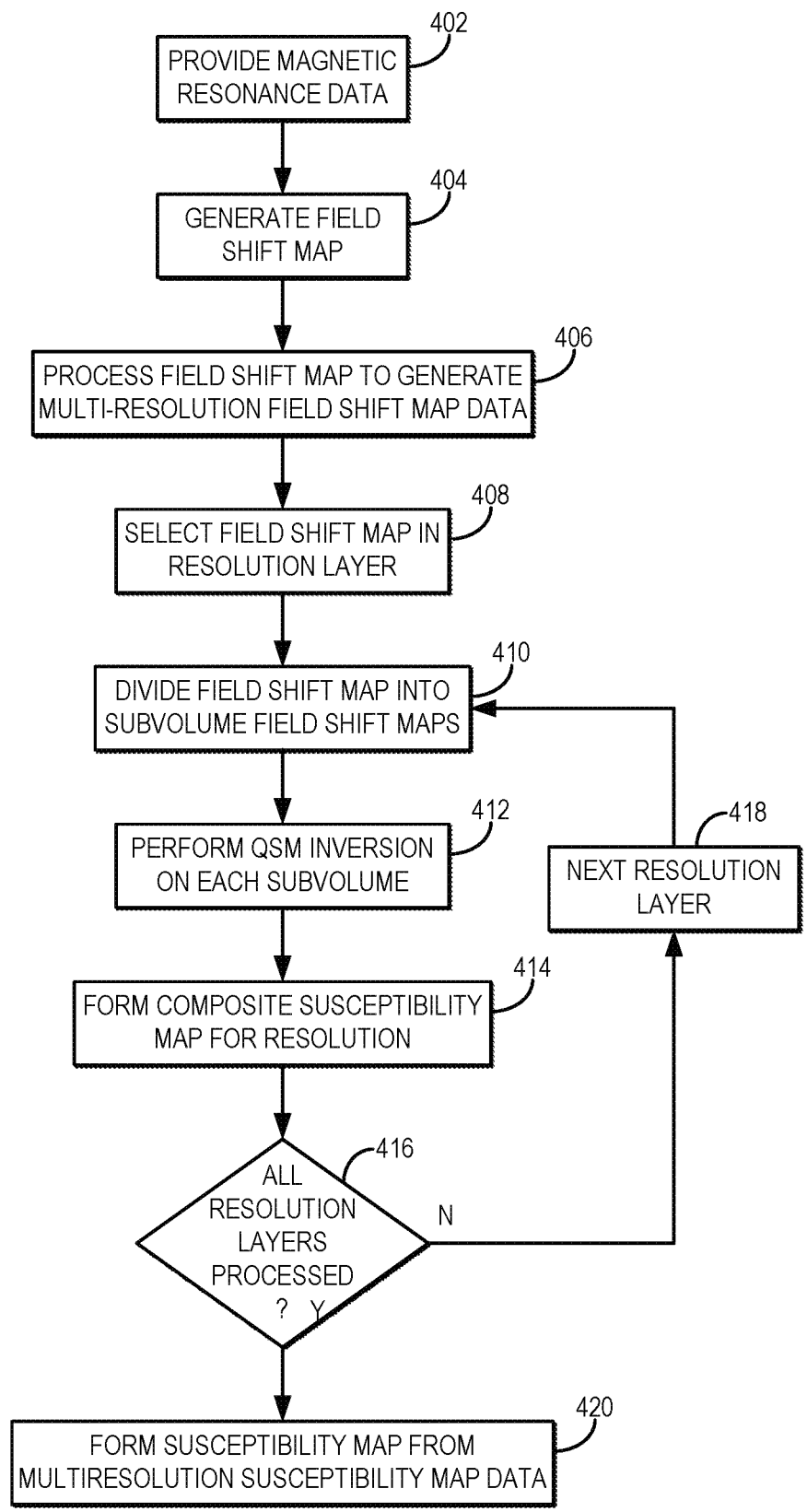
FIG. 4 is a flowchart setting forth the steps of an example method for generating a quantitative susceptibility map using localized processing of multiresolution field shift map data.

Referring now to FIG. 4, a flowchart is illustrated as setting forth the steps of an example method for producing a quantitative susceptibility map using multi-resolution parcellated volume processing to take advantage of localized field shift information for computing regional susceptibility distributions. The method includes providing magnetic resonance data to be processed, as indicated at step 402. As one example, the magnetic resonance data can be provided by retrieving previously acquired data from data storage. As another example, magnetic resonance data can be acquired with an MRI system and provided to a computer system, such as the MRI system workstation or other suitable computer system, for processing. In either case, the magnetic resonance data are suitable for generating quantitative susceptibility maps. For instance, the magnetic resonance data can include susceptibility-weighted data acquired using a suitable pulse sequence, such as a $T_2^*$-weighted pulse sequence or other pulse sequence capable of producing enhanced image contrast in areas with different susceptibility than surrounding tissue.

The provided magnetic resonance data are then processed to generate a field shift map, as indicated at step 404. The field shift map, $\delta$, indicates regions where field offsets resulting from significant differences in local magnetic susceptibility are present. The field shift map, $\delta$, is then processed to generate multiresolution field shift map data by generating a plurality of field shift maps each having a different spatial resolution, as indicated at step 406. Each different spatial resolution corresponds to a different resolution layer that will be separately processed to generate parcellated, local field shift maps, as described below in more detail. The different resolutions may correspond to voxels with 1 mm$^3$, 5-7 mm$^3$, and 15 mm$^3$ spatial resolution; though, it will be appreciated that any suitable spatial resolution or combination of spatial resolutions can be implemented. As one example, the multiresolution field shift map data can be generated by applying a sequence of blurring and residual propagation operations to the input field shift map to generate the plurality of field shift maps at different spatial resolutions. In such instances, the matrix dimensions of each resolution layer can be successively reduced by subtractions (e.g., subtractions of four or other numbers) in each dimension. As another example, wavelet transforms can be applied to the input field shift map to generate the multiresolution field shift maps for the different resolution layers.

The field shift maps contained in the multiresolution field shift map data are separately processed. Thus, as indicated at step 408, a field shift map for one of the resolution layers in the multiresolution field shift map data is selected for processing. The selected field shift map is then divided, or parcellated, into a number of field shift subvolumes, $\delta_{k,j}$, for the selected resolution layer, as indicated at step 410, thereby generating a plurality of local field shift maps for the selected resolution layer. The local field shift maps can be generated for the same subvolumes in each resolution layer, or can alternatively be generated for different subvolumes in different resolution layers. QSM inversion is then performed on the subvolumes in the selected resolution layer in order to produce quantitative susceptibility maps for each of the subvolumes in the selected resolution layer, as indicated at step 412. The parcel maps generated in this process thus represent quantitative susceptibility maps corresponding to regions of local susceptibility associated with the subvolumes, $V_{k,j}$, in each particular resolution layer.

In some implementations, a trained neural network or other machine learning algorithm is provided and used to produce susceptibility maps for the subvolumes, similar to the methods described above. As noted, the trained neural network or other machine learning algorithm can be implemented on a hardware processor and memory, and is trained on training data that are similar to the subvolume field shift maps. For instance, the training data can include parcels of data having similar size and resolution to those produced in step 408. As mentioned above, the training data can include parcellated field shift maps based on data acquired from the same subject as the magnetic resonance data provided in step 402, parcellated field shift maps obtained from a different subject, an average of parcellated field shift maps obtained from a population of subjects, EM simulation data including parcellated field shift maps simulated using one or more different forward models, or random susceptibility volumes. A specific, but non-limiting, embodiment of the EM simulation training approach utilizes existing in-vivo susceptibility estimates to generate random susceptibility distributions that possess the same spatial harmonic power spectrum or signatures, as the in-vivo data.

As noted, the machine learning algorithm can include a neural network, such as a convolutional neural network, or other suitable machine learning algorithm, such as support vector machines ("SVM") and other algorithms based on supervised learning, unsupervised learning, deep learning, ensemble learning, dimensionality reduction, and so on.

The quantitative susceptibility maps for the different subvolumes in a given resolution layer are then combined to form a composite quantitative susceptibility map for that resolution layer, as indicated at step 414, thereby generating multiresolution susceptibility map data. The composite susceptibility map can be a data structure stored in a memory, such as an image matrix whose pixels or voxels store quantitative magnetic susceptibility values for different spatial locations in an imaging volume. As one example, the individual parcel maps can be stitched together to form the composite map. The stitching procedure may include scaling the parcel maps, adjusting mutual information of the overlapping regions of the parcel maps, and adjusting the dynamic range of the parcel maps, as described above in more detail.

A determination is then made at decision block 416 whether the desired number of resolution layers have been processed to generate a composite susceptibility map corresponding to that resolution layer. If not, then the next resolution layer is selected at step 418 and the field shift map in that resolution layer is processed according to steps 410-414 to produce a composite susceptibility map for that resolution layer. When the desired amount of resolution layers have been processed, the resulting composite susceptibility maps are stored as multiresolution susceptibility map data.

The composite susceptibility maps for the different resolution layers are then combined to generate a susceptibility map for the subject, as indicated at step 420. As one example, the susceptibility map can be generated by performing the inverse of those operations that converted the input field shift map into the multiresolution field shift map data. For instance, when a wavelet transform is used to generate the multiresolution field shift map data, an inverse wavelet transform can be used to generate the susceptibility map from the multiresolution susceptibility map data. When the multiresolution field shift map data are generated using successive blurring operations, the susceptibility map can be generated through weighted superpositions of the multiresolution susceptibility map data. The susceptibility map can be stored for later processing and use, and can also be provided to a display for a clinician or other user.

Figure 5:
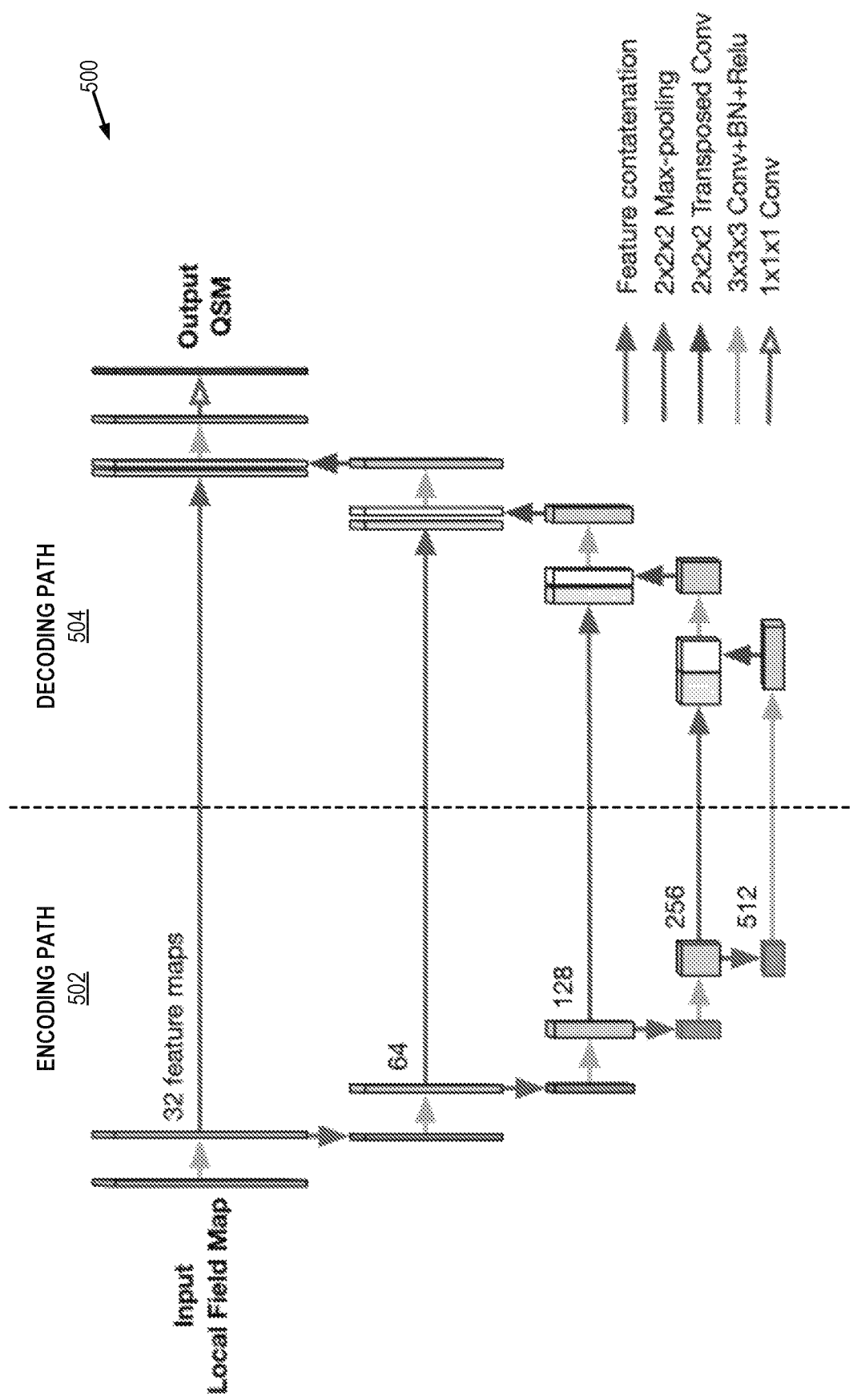
FIG. 5 is an example of an encoder-decoder neural network architecture that can be implemented by the systems and methods described in the present disclosure.

As noted above, in some instances the trained neural network can be an encoder-decoder neural network, such as a three-dimensional encoder-decoder deep neural network. An example of such a neural network is shown in FIG. 5. The data input to the network 500 are the local field shift maps and the data output are estimates of the source magnetic susceptibility tensor at each input voxel. In this example, the applied encoder-decoder network architecture utilizes skip connections between the encoding path 502 and decoding path 504, which can effectively transfer local feature information from the encoding path to the decoding path and facilitate faster training.

The encoding path 502 generally implements a convolutional neural network. For instance, the encoding path 502 can include repeated application of convolutional layers (e.g., 3×3×3 convolutions) each followed by a batch normalization layer and a nonlinear layer, which may be a rectified linear unit ("ReLU"). The output of each convolutional layer is a feature map that is passed to the nonlinear layer. Each feature map generally represents a particular feature extracted at all locations on the input. Each nonlinear layer is followed by a downsampling layer, which may be a pooling layer, such as a max pooling layer (e.g., a max pooling layer using stride 2×2×2), an average pooling layer, an L2-norm pooling layer, or so on. The output of each nonlinear layer is a feature map that is passed to the downsampling layer. At each downsampling step, the number of feature channels in the feature map can be doubled, or otherwise increased.

The decoding path 504 generally includes a transposed convolutional layer with additional feature concatenation layers from the encoding layers. The output of each transposed convolutional layer is a feature map that is passed to the concatenation layer. At each transposed convolution step, the number of feature channels in the feature map can be halved, or otherwise reduced. As noted, each upsampled feature map is also concatenated with the corresponding feature map from the encoding path 502. The concatenated feature map is then passed to a convolutional layer followed by a batch normalization layer and a nonlinear layer (e.g., a ReLU). The output of the convolutional layer is a feature map that is passed to the batch normalization layer, the output of which is a feature map passed to the nonlinear layer. The final layer is a convolutional layer (e.g., a 1×1×1 convolution) with linear activation, which is applied to output the susceptibility estimations.

As one example, the encoder-decoder network shown in FIG. 5 was trained using an L1 loss function and ADAM optimizer. The initial learning rate in this example was set as 0.001, with an exponential decay of the rate occurring at every 200 steps with a time constant of 0.9. Due to the deep nature of this neural network and the heavy computation required to train it, 10,000 datasets were used for training each model with batch size 8.

Due to the different target QSM map resolutions for each of the test scenarios, two encoder-decoder network models were trained in this example. For a dataset with voxel size isotropic 1.06 mm, the network was trained to independently invert 3D parcels of 128×128×128 voxels. For another dataset with voxel size 0.5×0.5×2.0 $mm^3$, the network was trained to invert 3D parcels of 192×192×64 voxels. In the prediction stage, segmentation of full-resolution input volumes into the parcels with parcel size equal to neural network input data size was performed using 32×32×32 overlap regions. After QSM inference using the trained encoder-decoder networks, the parcels were combined to form a composite image. In order to avoid edge artifacts in the composite QSM maps, 8×8×8 voxel boundaries (within the 32×32×32 overlap region) were discarded before parcel combination. Linear regression utilizing the overlapping regions between parcels was used to adjust the relative scaling and bias between the individual parcels. Final QSM maps were then computed via k-space substitution. A hard threshold of 0.2 was utilized to define the region of k-space where the forward field map of QSM estimation was substituted into the k-space of input field map; however, other threshold values could be used in other instances. The k-space substitution can implement a dipole convolution of k-space data associated with the neural network output, a dipole convolution of k-space data associated with a direct inversion of field shift map data, or combinations thereof. After this substitution, inverse Fourier transformation yielded the final QSM estimate.

As noted above, the encoder-decoder neural network can be trained using multi-resolution training data, such that the encoder-decoder neural network is trained to different resolutions and parcel sizes. Training of the encoder-decoder neural network may, therefore, include training a different encoder-decoder neural network on each of the different resolution sizes, or may include training a single encoder-decoder neural network on more than one of the different resolution sizes.

Figure 6:
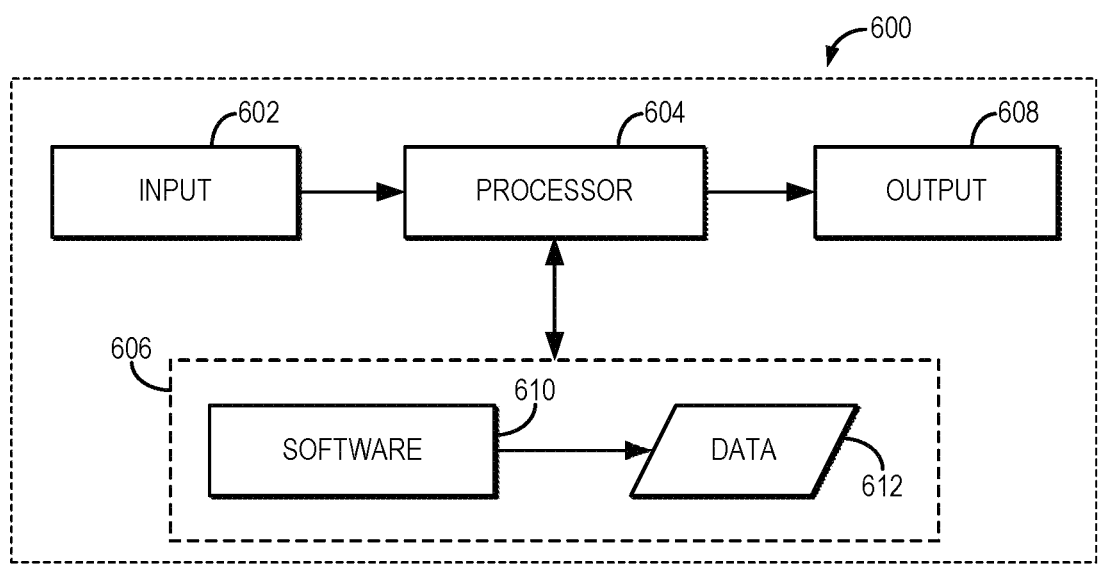
FIG. 6 is a block diagram of an example computer system that can implement the methods described here.

Referring now to FIG. 6, a block diagram of an example of a computer system 600 that can perform the methods described in the present disclosure is shown. The computer system 600 generally includes an input 602, at least one hardware processor 604, a memory 606, and an output 608. Thus, the computer system 600 is generally implemented with a hardware processor 604 and a memory 606.

The computer system 600 may also be implemented, in some examples, by a workstation, a notebook computer, a tablet device, a mobile device, a multimedia device, a network server, a mainframe, one or more controllers, one or more microcontrollers, or any other general-purpose or application-specific computing device. The one or more hardware processors 604 may also include graphical processing units ("GPUs") or other specialized image processing units.

The computer system 600 may operate autonomously or semi-autonomously, or may read executable software instructions from the memory 606 or a computer-readable medium (e.g., a hard drive, a CD-ROM, flash memory), or may receive instructions via the input 602 from a user, or any another source logically connected to a computer or device, such as another networked computer or server. Thus, in some embodiments, the computer system 600 can also include any suitable device for reading computer-readable storage media.

In general, the computer system 600 is programmed or otherwise configured to implement the methods and algorithms described in the present disclosure. For instance, the computer system 600 can be programmed to train neural networks or other machine learning algorithms, and to implement such algorithms on parcellated subvolumes of field shift maps, other magnetic resonance images, in order to generate quantitative susceptibility maps according to the methods described in the present disclosure. The computer system 600 can also be programmed to implement multi-resolution QSM inversion according to the methods described in the present disclosure.

The input 602 may take any suitable shape or form, as desired, for operation of the computer system 600, including the ability for selecting, entering, or otherwise specifying parameters consistent with performing tasks, processing data, or operating the computer system 600. In some aspects, the input 602 may be configured to receive data, such as data acquired with an MRI system, an MEG system, or other suitable medical imaging or measurement system. Such data may be processed as described above to generate parcellated subvolumes of data, whether of the same resolution or multiple different resolutions, and to perform source inversion of the parcellated subvolumes of data, whether using a machine learning algorithm or otherwise. In addition, the input 602 may also be configured to receive any other data or information considered useful for generating susceptibility maps or otherwise performing source inversion on input data using the methods described above.

Among the processing tasks for operating the computer system 600, the one or more hardware processors 604 may also be configured to carry out any number of post-processing steps on data received by way of the input 602.

The memory 606 may contain software 610 and data 612, such as data acquired with an MRI system, an MEG system, or other suitable medical imaging or measurement system, and may be configured for storage and retrieval of processed information, instructions, and data to be processed by the one or more hardware processors 604. In some aspects, the software 610 may contain instructions directed to training a neural network or other machine learning algorithm, generating parcellated subvolumes of data, generating multiresolution data, and implementing source inversion of the parcellated subvolumes, whether using a machine learning algorithm or otherwise.

In addition, the output 608 may take any shape or form, as desired, and may be configured for displaying images, including magnetic resonance images, susceptibility maps, parcellated subvolumes of data, and other desired information.

Figure 7:
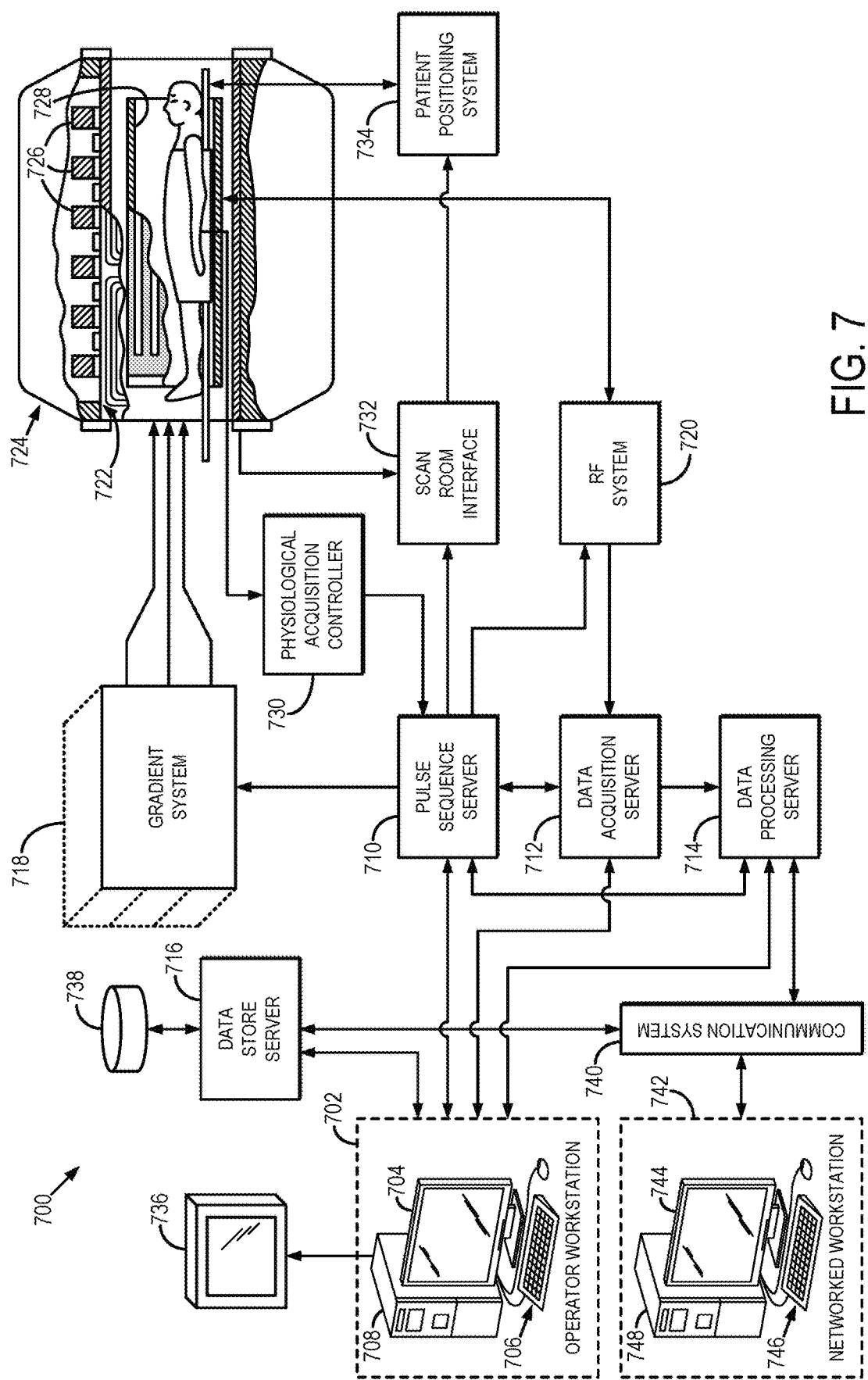
FIG. 7 is a block diagram of an example magnetic resonance imaging ("MRI") system that can implement the methods described here.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a quantitative susceptibility map using magnetic resonance imaging (MRI), the steps of the method comprising:
   (a) providing to a computer system, magnetic resonance data acquired with an MRI system;
   (b) generating with the computer system, a field shift map from the magnetic resonance data, the field shift map depicting susceptibility-induced resonance frequency shifts in a volume;
   (c) generating with the computer system, multiresolution field shift map data by processing the field shift map in order to generate a plurality of field shift maps each with a different spatial resolution associated with a different resolution layer;

(d) generating with the computer system for each resolution layer, local field shift map data by dividing the field shift map associated with a given resolution layer into a plurality of local field shift maps, each local field shift map corresponding to a subvolume of the volume;

(e) generating with the computer system for each resolution layer, a local susceptibility map for each subvolume by performing a quantitative susceptibility mapping inversion algorithm on each local field shift map associated with a given resolution layer using the computer system;

(e) forming with the computer system, multiresolution susceptibility map data by combining the local susceptibility maps for each resolution layer using the computer system in order to generate a plurality of composite susceptibility maps each depicting quantitative values of susceptibility in the volume for each resolution layer; and (f) forming a susceptibility map by combining the plurality of susceptibility maps in the multiresolution susceptibility map data.

2. The method as recited in claim 1, wherein the quantitative susceptibility mapping inversion algorithm performed in step (e) comprises a trained machine learning algorithm implemented with a hardware processor and memory of the computer system;

wherein the trained machine learning algorithm was trained on training data including a plurality of subvolume training data sets that have similar size and resolution as the plurality of local field shift maps; and wherein the training data store susceptibility-induced resonance frequency shift values.

3. The method as recited in claim 2, wherein the training data comprise one of:

another field shift map that has been divided into another plurality of local field shift maps each corresponding to one of the plurality of subvolume training data sets; or simulated data generated with a computer system using an electromagnetic model.

4. The method as recited in claim 2, wherein the trained machine learning algorithm is a trained neural network.

5. The method as recited in claim 4, wherein the trained neural network is a trained convolutional neural network.

6. The method as recited in claim 1, wherein the field shift map is processed using wavelet transforms to generate the multiresolution field shift map data.

7. The method as recited in claim 6, wherein the susceptibility map is generated by applying inverse wavelet transforms to the multiresolution susceptibility map data.

8. The method as recited in claim 1, wherein the field shift map is processed using successive blurring operations to generate the multiresolution field shift map data.

9. The method as recited in claim 8, wherein the susceptibility map is generated through weighted superpositions of the plurality of susceptibility maps in the multiresolution susceptibility map data.

10. A method for producing a quantitative susceptibility map using magnetic resonance imaging (MRI), the steps of the method comprising:

(a) providing to a computer system, magnetic resonance data acquired with an MRI system;

(b) generating with the computer system, a field shift map from the magnetic resonance data, the field shift map depicting susceptibility-induced resonance frequency shifts in a volume;

(c) dividing with the computer system, the field shift map into a plurality of local field shift maps, each local field shift map corresponding to a subvolume of the volume;

(d) providing to the computer system, a trained machine learning algorithm implemented with a hardware processor and memory of the computer system, wherein the trained machine learning algorithm is a machine learning algorithm that has been trained on training data including a plurality of subvolume training data sets that are similarly sized as the plurality of local field shift maps and that store susceptibility-induced resonance frequency shift values;

(e) applying the plurality of local field shift maps to the trained machine learning algorithm in order to generate with the computer system a local susceptibility map for each subvolume; and (e) forming a composite susceptibility map by combining the local susceptibility maps using the computer system, the composite susceptibility map depicting quantitative values of susceptibility in the volume;

wherein the trained machine learning algorithm is a trained neural network comprising a trained encoder-decoder neural network.

11. The method as recited in claim 10, wherein the training data comprise one of:

another field shift map that has been divided into another plurality of local field shift maps each corresponding to one of the plurality of subvolume training data sets; or simulated data generated with a computer system using an electromagnetic model.

12. The method as recited in claim 11, wherein the simulated data are generated with the computer system using the electromagnetic model such that the simulated data have a spatial harmonic power spectrum that is similar to in vivo susceptibility data.

13. The method as recited in claim 10, wherein applying the plurality of local field shift maps to the trained encoder-decoder neural network comprises passing the plurality of local field shift maps to an encoding path of the encoder-decoder neural network, generating output; and passing the output from the encoding path of the encoder-decoder neural network to a decoding path of the encoder-decoder neural network, generating the local susceptibility map for each subvolume.

14. The method as recited in claim 13, wherein passing the plurality of local field shift maps to the encoding path of the encoder-decoder neural network includes:

(i) passing each local field shift map to a convolutional layer, generating output;

(ii) passing the output from the convolutional layer to a batch normalization layer, generating output;

(iii) passing the output from the batch normalization layer to a nonlinear layer, generating output; and (iv) passing the output from the nonlinear layer to a downsampling layer, generating output.

15. The method as recited in claim 13, wherein passing the output of the encoding path of the encoder-decoder neural network to the decoding path of the encoder-decoder neural network includes:

(i) passing the output of the encoding path of the encoder-decoder neural network to a transposed convolutional layer, generating output;

(ii) passing the output from the transposed convolutional layer to a convolutional layer, generating output;
(iii) passing the output from the convolutional layer to a batch normalization layer, generating output; and
(iv) passing the output from the batch normalization layer to a nonlinear layer, generating output.

16. The method as recited in claim 10, wherein the trained machine learning algorithm simultaneously removes background field values while estimating the local susceptibility map for each subvolume, such that step (e) comprises applying the plurality of local field shift maps to the trained machine learning algorithm in order to generate with the computer system the local susceptibility map for each subvolume in which errors associated with background field values have been reduced.

17. The method as recited in claim 10, wherein at least one of the plurality of local susceptibility maps or the composite susceptibility map are further processed using a k-space substitution process that implements a dipole convolution.

18. A method for producing a quantitative susceptibility map using magnetic resonance imaging (MRI), the steps of the method comprising:
(a) providing to a computer system, magnetic resonance data acquired with an MRI system;
(b) generating with the computer system, a field shift map from the magnetic resonance data, the field shift map depicting susceptibility-induced resonance frequency shifts in a volume;
(c) providing to the computer system, a trained machine learning algorithm implemented with a hardware processor and memory of the computer system, wherein the trained machine learning algorithm is a machine learning algorithm that has been trained on training data including training data that are similarly sized as the field shift map and that store susceptibility-induced resonance frequency shift values; and
(d) applying the field shift map to the trained machine learning algorithm in order to generate with the computer system a susceptibility map for the volume;
wherein the training data comprise simulated data generated with a computer system using an electromagnetic model such that the simulated data have a spatial harmonic power spectrum that is similar to in vivo susceptibility data.

19. The method as recited in claim 18, further comprising:
dividing with the computer system, the field shift map into a plurality of local field shift maps, each local field shift map corresponding to a subvolume of the volume;
applying the plurality of local field shift maps to the trained machine learning algorithm in order to generate with the computer system a local susceptibility map for each subvolume; and
forming a composite susceptibility map by combining the local susceptibility maps using the computer system, the composite susceptibility map depicting quantitative values of susceptibility in the volume.

20. A method for producing a quantitative susceptibility map using magnetic resonance imaging (MRI), the steps of the method comprising:
(a) providing to a computer system, magnetic resonance data acquired with an MRI system;
(b) generating with the computer system, a field shift map from the magnetic resonance data, the field shift map depicting susceptibility-induced resonance frequency shifts in a volume;
(c) dividing with the computer system, the field shift map into a plurality of local field shift maps, each local field shift map corresponding to a subvolume of the volume;
(d) providing to the computer system, a trained machine learning algorithm implemented with a hardware processor and memory of the computer system, wherein the trained machine learning algorithm is a machine learning algorithm that has been trained on training data including a plurality of subvolume training data sets that are similarly sized as the plurality of local field shift maps and that store susceptibility-induced resonance frequency shift values;
(e) applying the plurality of local field shift maps to the trained machine learning algorithm in order to generate with the computer system a local susceptibility map for each subvolume; and
(e) forming a composite susceptibility map by combining the local susceptibility maps using the computer system, the composite susceptibility map depicting quantitative values of susceptibility in the volume
wherein the training data comprise simulated data generated with a computer system using an electromagnetic model such that the simulated data have a spatial harmonic power spectrum that is similar to in vivo susceptibility data.

* * * * *

UNITED STATES PATENT AND TRADEMARK OFFICE
CERTIFICATE OF CORRECTION

PATENT NO. : 11,372,066 B2
APPLICATION NO. : 16/968534
DATED : June 28, 2022
INVENTOR(S) : Kevin M. Koch et al.

It is certified that error appears in the above-identified patent and that said Letters Patent is hereby corrected as shown below:

In the Specification

Column 7, Line 24, "$\lambda$" should be --$\chi$--.

Column 8, Line 52, "$\delta_{k,j}$" should be --$\delta_{k,l}$--.

Column 8, Line 65, "$V_{k,j}$" should be --$V_{k,l}$--.

Signed and Sealed this
Twenty-third Day of August, 2022

Katherine Kelly Vidal
*Director of the United States Patent and Trademark Office*